US00PP26541P3

(12) United States Plant Patent
Cain

(10) Patent No.: US PP26,541 P3
(45) Date of Patent: Mar. 29, 2016

(54) GRAPEVINE 'IFG TWENTY-ONE'

(50) Latin Name: ***Vitis interspecific* hybrid**
Varietal Denomination: IFG Twenty-one

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 114 days.

(21) Appl. No.: 14/120,644

(22) Filed: Jun. 12, 2014

(65) Prior Publication Data

US 2015/0366118 P1 Dec. 17, 2015

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Twenty-one'. The new grapevine is characterized by producing small naturally seedless red berries having an elliptic shape with a unique combination of muscat and labrusca flavor. The strong fruity flavor is reminiscent of strawberries. Fruits normally ripen very early season about early to mid-July near Delano Calif. Fruits are fairly low in acidity, with medium dense, firm texture. Berries color readily even in hot climatic conditions and produce completely colored bright red berries.

1 Drawing Sheet

Latin name of the genus and species claimed: *Vitis* interspecific hybrid.

Variety denomination: 'IFG TWENTY-ONE'.

BACKGROUND OF THE INVENTION

The new and distinct grapevine described and claimed herein originated from a hand pollinated cross of the 03003-074-251 (unnamed interspecific selection from the IFG breeding program) and the 02089-081-217 (unnamed selection from the IFG breeding program) hybridized in May 2006. The abortive seed traces were subsequently embryo cultured and the resulting population of plants was planted in the field in April 2007. The present variety of grapevine was selected as a single plant in July 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Twenty-one' is characterized by producing small naturally seedless red berries having an elliptic shape with a unique combination of muscat and labrusca flavor. The strong fruity flavor is reminiscent of strawberries. Fruits normally ripen very early season about early to mid-July near Delano Calif. Fruits are fairly low in acidity, with medium dense, firm texture. Berries color readily even in hot climatic conditions and produce completely colored bright red berries. Vines are very productive and can be pruned to short spurs. Clusters are large, slightly tight, and require tipping, thinning and sizing with gibberellic acid to enlarge berry size. The new grapevine differs from its maternal parent the 03003-074-251 selection by having red rather than light green berries and by having an elliptic berry shape as opposed to an ovate shape of the 03003-074-251. 'IFG Twenty-one' has smaller seed traces and a broader more conical cluster than its maternal parent. 'IFG Twenty-one' can be distinguished from its pollen parent, 02089-081-217, by a light red color as opposed to dark red to black color, by having medium firm, slightly less dense flesh, by having a slightly larger seed trace, and by having a combination of muscat and labrusca flavor rather than a neutral *vinifera* flavor of the 02089-081-217.

Grape breeders have used several native American grape species to improve hardiness, disease and insect resistance as well as incorporate aromatic flavors into the *vinifera* species. Previously introduced interspecific varieties have had very limited commercial success due to small fruit size, large seed traces, slipskin texture or lack of firmness. The new grapevine variety is being introduced because of its unique combination of muscat and labrusca flavor combined with firm texture, seedlessness, good adhesion of skin and flesh and excellent coloring characteristics.

BRIEF DESCRIPTION OF THE FIGURE

The accompanying photographic illustration in FIG. 1 illustrates in full color 'IFG Twenty-one'.

The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-one' plants grown in the vicinity of Delano, Kern County, Calif. during 2011 and 2012, and is believed to apply to plants of the variety grown under similar conditions of soil and climate elsewhere:

Vine:

*General.*—Size — Large. Vigor — Vigorous. Density of foliage — Dense. Productivity — Productive. Root stock — Own root. Training method — Typically spur pruned leaving 2 bud spurs.

*Trunk.*—Trunk diameter of 4-year-old vines at 30 cm above the soil line — About 5.0 cm. Shape — Medium. Straps — Short-split. Surface texture — Medium. Inner bark color — Can be any of the following colors; Greyed orange; 165A, and 166B and C.

Shoots:

*Young shoot.*—Form of tip — Wide open. Distribution of anthocyanin coloration of tip — Absent. Intensity of anthocyanin coloration of tip — Absent. Density of prostrate hairs of tip — Dense. Density of erect hairs of tip — Absent. Color — Can be any of the following colors; Green; 144A and B, and 146B and C.

*Woody shoot* (*mature canes*).—Shape — Stocky. Internode length — Medium; About 8.7 cm. Width at node — About 0.9 cm. Cross section — Elliptic. Surface — Striate. Main color — Can be any of the following colors; Greyed orange; 164A and B, and 165A. Density of erect hairs on nodes — None. Density of erect hairs on internodes — None. Growth of axillary shoots — Weak to medium; Approximately 5.4 cm.

*Flowering shoot.*—Vigor during flowering — Medium to Strong. Attitude during flowering on shoots not tied — Semi-drooping to Drooping. Color — dorsal side of internodes — Green. Color — ventral side of internodes — Green. Color — dorsal side of nodes — Green. Color — ventral side of nodes — Green. Density of prostrate hairs of nodes — Sparse. Density of erect hairs of nodes — None. Density of prostrate hairs on internode — Very sparse. Density of erect hairs on internode — None. Anthocyanin coloration of buds — Present.

*Tendrils.*—Distribution on the shoot (at full flowering) — Discontinuous. Length of Tendril — Medium; About 17.8 cm. Thickness — Medium. Color — Can be any of the following colors; Green; N144A and 144B. Form — Bifurcated and trifurcated. Number of consecutive tendrils — 2.

Leaves:

*Young leaves.*—Color of upper surface of first four distal unfolded leaves — Green. Average intensity of anthocyanin coloration of six distal leaves prior to flowering — Weak. Density of prostrate hairs between veins (lower surface) — Very dense. Density of prostrate hairs on veins (lower surface) — Very dense. Density of erect hairs between veins (lower surface) — Absent. Density of erect hairs on veins (lower surface) — Absent.

*Mature leaves.*—Average length — About 15.8 cm. Average width — About 18.3 cm. Mature leaf size — Medium. Shape of blade — Wedge-shaped. Number of lobes — 5 to 7. Anthocyanin coloration of main veins on upper side of blade — Weak. Mature leaf profile — Undulate. Blistering surface of blade upper surface — Very weak. Leaf blade tip — In the plane of the leaf. Undulation of margin — Medium. Thickness — Medium. Undulation of blade between main and lateral veins — Overall. Shape of teeth — Both sides concave. Length of teeth — Medium. Ratio length/width of teeth — Medium. Shape of upper lateral sinuses — Strongly overlapping. Depth of upper lateral sinuses — Deep. General shape of petiole sinus — Lobes strongly overlapping. Shape of base of upper leaf sinuses — V-shaped. Tooth at petiole sinus — Absent. Density of prostrate hairs between veins on lower surface of blade — Medium. Density of erect hairs between veins on lower surface of blade — Sparse. Density of prostrate hairs on main veins on lower surface of blade — Medium. Density of erect hairs on main veins on lower surface of blade — Sparse to medium. Density of prostrate hairs on main veins on upper surface of blade — Sparse. Density of erect hairs on main veins on upper surface of blade — Very sparse to sparse. Autumn coloration of leaves — Leaves can be a single color or combination of colors, in a mottled pattern or on the edges of the leaves; Yellow; 13A and B, and Yellow orange; 15B and C, and Orange red; N34A, and Greyed purple; N180A and B and C.

*Upper surface.*—Color — Can be any of the following colors; Green; 139A, and 137A, and 147A. Anthocyanin coloration of main veins — Weak. Surface appearance — Semi-glossy. Blistering surface of blade — Very weak.

*Lower surface.*—Color — Can be any of the following colors; Green; 138A, and 137B and C, and N138B. Anthocyanin coloration of main veins (lower surface) — Weak. Glossiness — Weak. Surface texture — Rugose. Surface appearance — Semi-glossy.

*Petiole.*—Length — About 15.5 cm. Length of petiole compared to middle vein — Equal. Density of prostrate hairs on petiole — Sparse. Density of erect hairs on petiole — None.

*Buds.*—Bud fruitfulness — Basal: Mostly fruitful. Position of first fruitful shoot on previous season cane — $1^{st}$ to $2^{nd}$ node. Time of bud burst — Early; Mar. 12, 2012.

Flowers:

*General.*—Flower sex — Hermaphrodite. Length of first inflorescence — Medium; About 18.7 cm long by 7.4 cm wide. Position of first flowering and fruiting node — $2^{nd}$ through $4^{th}$ node (current season growth). Number of inflorescence per flowering shoot — 1.1 to 2. Time of bloom — Midseason as compared with similar varieties in the growing area of Delano, Calif. Date of full bloom — May 15, 2012.

Fruit:

*General.*—Ripening period — Very early; Approximately Jul. 18, 2012. Use — Fresh market. Keeping quality — Medium. Resistance to — Insects: Average typical of *Vitis vinifera* species. Diseases: Average typical of *Vitis vinifera* species. Refractometer test — soluble solids: About 19.0 Brix. Brix/acid — About 36.5. Titratable acidity — About 0.52. Juice pH — About 3.5.

*Cluster.*—Mature cluster length (peduncle excluded) — About 26.1 cm. Mature cluster width — About 17.6 cm. Mature cluster weight — About 750 g. Bunch density — Medium to dense. Number of berries — About 255. Form — Conical.

*Peduncle.*—Lignification of peduncle — Weak. Length of peduncle — Short; Approximately 2.2 cm.

*Berry.*—Uniformity of size — Slightly Variable. Single berry weight — About 3.4 g natural; to about 3.9 g when treated with gibberellic acid. Shape — Elliptic. Seeds — Contains small rudimentary seed traces not noticeable. Cross section — Circular. Berry dimensions — Longitudinal axis: About 1.9 cm. Horizontal axis: About 1.7 cm. Berry firmness — Medium. Particular flavor — Combination of Muscat and Labrusca reminiscent of strawberries. Bloom (cuticular wax) — Medium. Berry separation from pedicel — Difficult. Skin color (without bloom) — About Red-Purple Group 59A.

*Skin.*—Thickness — Medium. Texture — Medium. Reticulation — Absent. Tenacity — Tenacious to flesh.

What is claimed:

1. A new and distinct variety of grapevine as herein illustrated and described.

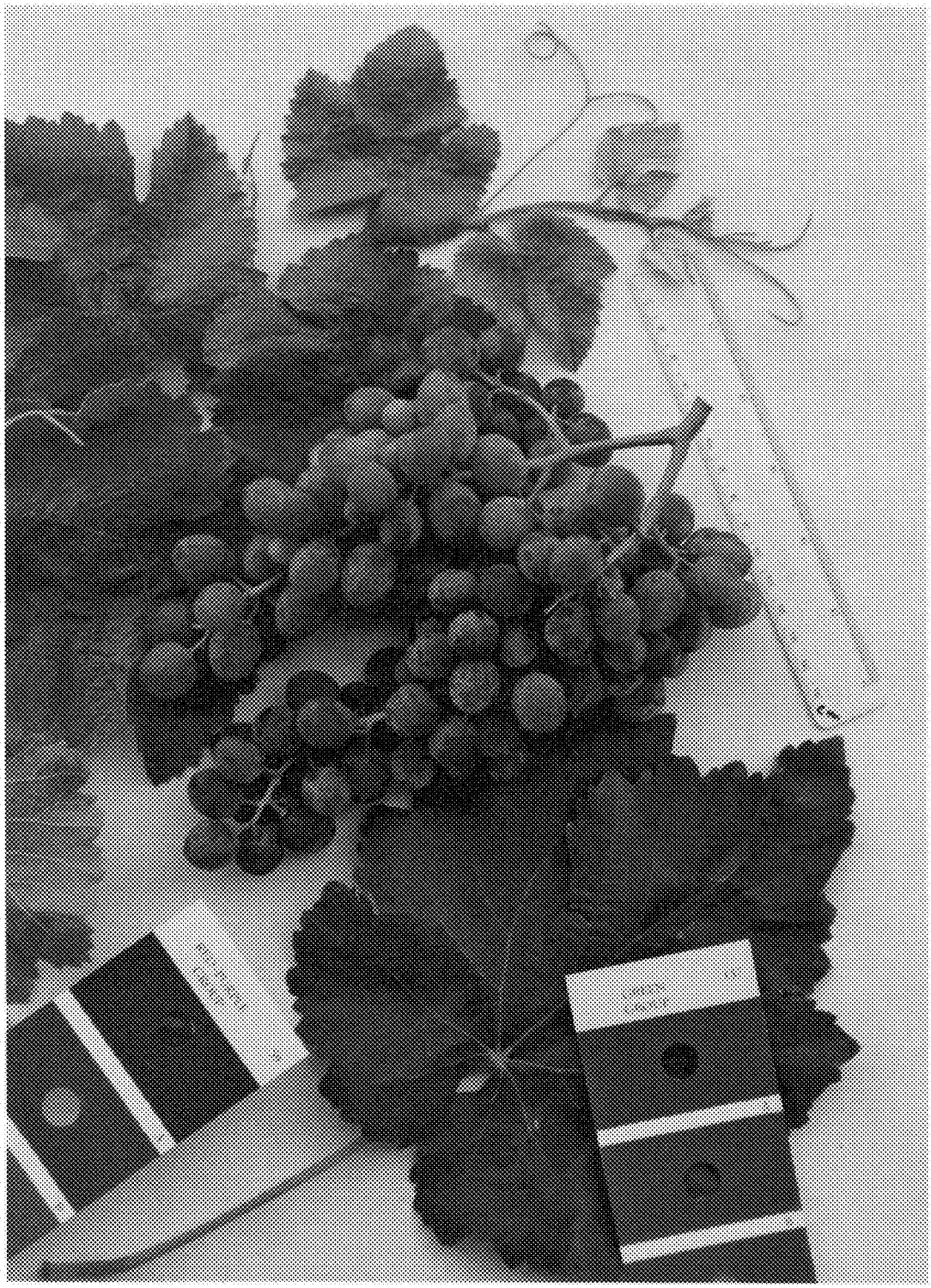

* * * * *